United States Patent
Yang et al.

(10) Patent No.: US 9,642,781 B2
(45) Date of Patent: May 9, 2017

(54) GLASS FILLERS FOR COMPOSITES

(71) Applicant: Heraeus Kulzer GmbH, Hanau (DE)

(72) Inventors: Wenling Yang, Beijing (CN); Hengchang Xu, Beijing (CN); Andreas Utterodt, Neu Anspach (DE)

(73) Assignee: HERAEUS KULZER GMBH, Hanau (DE)

( * ) Notice: Subject to any disclaimer, the term of this patent is extended or adjusted under 35 U.S.C. 154(b) by 0 days.

(21) Appl. No.: 14/888,900

(22) PCT Filed: May 13, 2014

(86) PCT No.: PCT/EP2014/059789
§ 371 (c)(1),
(2) Date: Nov. 3, 2015

(87) PCT Pub. No.: WO2014/184203
PCT Pub. Date: Nov. 20, 2014

(65) Prior Publication Data
US 2016/0081886 A1    Mar. 24, 2016

(30) Foreign Application Priority Data
May 15, 2013   (EP) .................................... 13167781

(51) Int. Cl.
*A61K 6/00*    (2006.01)
*C03B 19/10*   (2006.01)

(52) U.S. Cl.
CPC .......... *A61K 6/0091* (2013.01); *A61K 6/0005* (2013.01); *A61K 6/0008* (2013.01); *C03B 19/108* (2013.01)

(58) Field of Classification Search
CPC .. A61K 6/0091; A61K 6/0008; A61K 6/0005; C03B 19/108
USPC ................ 428/402; 501/11, 32, 53; 65/21.1
See application file for complete search history.

(56) References Cited

U.S. PATENT DOCUMENTS

| | | | |
|---|---|---|---|
| 4,389,497 A | 6/1983 | Schmitt et al. | |
| 4,906,446 A * | 3/1990 | Engelbrecht | A61K 6/083 423/335 |
| 5,707,440 A * | 1/1998 | Hengchang | A61K 6/083 106/35 |
| 2005/0234148 A1 * | 10/2005 | Ruppert | A61K 6/0091 523/116 |
| 2008/0160206 A1 * | 7/2008 | Burtscher | A61K 6/0073 427/450 |

FOREIGN PATENT DOCUMENTS

| | | | |
|---|---|---|---|
| CA | 2254355 A1 | | 5/2000 |
| DE | 19757645 | * | 6/1999 |
| DE | 19757645 A1 | | 6/1999 |

OTHER PUBLICATIONS

European Search Report for corresponding EP application 13167781.7-1501 dated Oct. 25, 2013.
International Search Report and Written Opinion of the International Searching Authority for corresponding PCT Application PCT/EP2014/059789 dated Jul. 9, 2014.

* cited by examiner

*Primary Examiner* — Leszek Kiliman
(74) *Attorney, Agent, or Firm* — Norris McLaughlin & Marcus PA (57) ABSTRACT

The invention relates to a particulate glass filler wherein glass particles of 0.2 to 1 μm mean particle size are connected with other particles, the connection being effected by the glass material itself. More precisely particulate glass filler comprising glass particles, wherein the particles contains centrally located macro glass particles and on the outer surface located micro glass particles wherein the macro and micro glass particles are connected by the material of said particles. Further the invention relates to a method for manufacturing the glass particles and the particulate glass filler comprising said glass particles. It also relates to a composite or dental material comprising the above particulate glass filler.

20 Claims, 7 Drawing Sheets

GLASS FILLERS FOR COMPOSITES

This application is a §371 U.S. National stage of PCT International Patent Application No. PCT/EP2014/059789, filed May 13, 2014, which claims foreign priority benefit of European Patent Application No. EP 13167781.7, filed May 15, 2013, the disclosures of each of which patent applications are incorporated herein by reference.

FIELD OF THE INVENTION

The invention relates to a particulate glass filler, a method for producing it and its use in dental composite materials. The invention relates to a particulate glass filler wherein glass particles of 0.2 to 1 µm mean particle size are connected with other particles, the connection being effected by the glass material itself. More precisely particulate glass filler comprising glass particles, wherein the particles contains centrally located macro glass particles and on the outer surface located micro glass particles wherein the macro and micro glass particles are connected by the material of said particles. Further the invention relates to a method for manufacturing the glass particles and the particulate glass filler comprising said glass particles. It also relates to a composite or dental material comprising the above particulate glass filler.

BACKGROUND

In the field of tooth filling materials which are cured by polymerization it was considered to be a great step forward when Rafael L. Bowen introduced long-chain monomeric dimethacrylate re-action products of bisphenol A and its derivatives with glycidyl methacrylate, in particular the so-called bis-GMA; and fine quartz glass powder for reinforcement of the plastic matrix in place of the methyl methacrylate used up to then (U.S. Pat. No. 3,066,112).

A further example of a dental material containing, in addition to organic monomers, a finely divided inorganic filler is described in U.S. Pat. No. 3,539,533. The polymerizable binder in this case is a mixture of bis-GMA, bisphenol A-dimethacrylate, diluted monomers, in particular triethylene glycol dimethacrylate and, if required, methacrylic acid in small amounts which is used, together with approximately 65 to 75 weight-% of the inorganic filler, for example silicon dioxide, glass, aluminum oxide or quartz. The inorganic filler can be of a particle size of approximately 2 to 85 micrometers; for improving the bond between filler and resin/filler is pretreated with silane, for example 3-methacryloyl oxypropyl trimethoxysilane.

Fillings for teeth, caps, artificial teeth and the like, having good mechanical properties, can be produced from dental materials (composites) containing inorganic fillers of the most varied chemical composition—mainly of glass, ceramic materials or glass-ceramic materials which have been treated with silane materials to improve the adhesion between filler and resin.

The use of micro-fine inorganic fillers with average particle sizes between 0.01 to 0.4 micrometers also resulted in dental plastic products which were improved in the esthetic sense. These products could be polished to a high gloss and have a transparency similar to that of natural teeth (DE 24 03 211 C3).

The so-called hybrid materials represent a further step in the development of resin based dental materials which contain micro-fine fillers as well as conventional fillers (macro fillers). Such a dental material is known, for example, from DE 24 05 578 C3. It contains 30 to 80 weight-% of a mixture of amorphous silicic acid produced by means of flame hydrolysis (pyrogenous silicon dioxide) of a maximum particle size of 0.07 micrometers and finely divided glass, preferably boron silicate glass, glass containing barium oxide or lanthanum oxide or lithium aluminum silicate glass of a particle size of up to 5 micrometers.

The dental filler described in DE 34 03 040 C2 contains 60 to 90 weight-% of a filler mixture of 5 to 20 weight-% of a filler opaque to X-rays with a particle size distribution between 0.5 and 40 micrometers, 20 to 35 weight-% of a filler opaque to X-rays with a particle size distribution between 0.2 and 15 micrometers and 45 to 75 weight-% of a silicon dioxide micro-filler with a particle size distribution between 5 and 150 nanometers.

A further example of a hybrid material is the dental material described in EP 382 033 A2 which contains, in addition to polymerizable acrylates or methacrylates and a catalyst for photo-polymerization (photo activator), 5 to 80 weight-% of silanized glass or silanized glass-ceramics with a mean particle size between 0.1 and 10 micrometers and 2 to 10 weight-% of a surface-treated micro-filler. The inorganic fillers used for reinforcing resin based dental materials mostly have a surface treated with a silane, for example 3-methacryloyl oxypropyl trimethoxy silane, which improves the compatibility with the organic components (DE 34 03 040 C2) and causes a chemical adhesion between the filler and the plastic matrix. A further improvement of the filler/plastic bond can be achieved when the possibility of a physical adhesion exists in addition to the chemical adhesion. In accordance with a proposal in U.S. Pat. No. 4,215,033, for example, physical adhesion can be provided by the use of a semi-porous filler obtained by etching a two-phase glass.

U.S. Pat. No. 5,707,440 A describes larger filler particles which are covered by smaller particles of different material. The larger particles have a lower melting point than the small particles and are typically glass particles. Thus when softened in the melting range, the larger particles are covered by the higher melting smaller particles. After cooling the particles keep sticking together and form a special kind of filler particles as illustrated in FIG. 1 of U.S. Pat. No. 5,707,440 A.

However, due to its construction from 2 kinds of inorganic filler with different refractive index, its disadvantage is the limited translucency of resulting composites that is not suitable for aesthetic restorations. The dimension of the $SiO_2$ surface decorated dental glass filler is determined by the central glass particle. Bigger particles of this type can not provide an improved gloss stability in comparison to conventional submicrohybrid composites.

Microfiller composites were developed to perform excellent esthetic properties, based on special pre-polymerized filler particles made from fumed silica (e.g. Aerosil . . . ) and suitable (meth)acrylate crosslinkers (e.g. DCDMA, DDMA, . . . ) by industrial polymerization and grinding. Such microfiller composite materials are appreciated due to their permanent gloss stability. Commonly most successful sub-microhybrid composites and nano-hybrid composites can not provide this advantage. An issue of the microfiller composites is the limited flexural strength below 100 MPa that allows only anterior restorations of class III (and class IV with limitations). Moreover microfiller composites do not provide any radio-opacity due to the filler load of fumed silica only.

A new filler technology was introduced with FILTEK by 3M-ESPE using agglomerated nanoparticles prepared by a thermal procedure probably. The resulting agglomerated filler particles are softer than compact dental glass fillers with a comparable size. The FILTEK fillers mimic the construction of fumed silica, which is also build of silica nano-agglomerates, but FILTEK fillers are constructed stronger from $SiO_2$ (and $ZrO_2$ to provide a radio-opacity) and improved mechanical performance of the composite. A higher content of Zirconia is necessary to increase the level of radio-opacity but on the other hand brings the disadvantage to reduce translucency at the same time.

OBJECTS OF THE INVENTION

It is therefore an object of the invention to provide a finely divided inorganic filler for which is retained in the surface of the plastic matrix even after extended abrasive action has occurred to wear away the surface of the plastic matrix filled with the inorganic filler particles. The filler particles should conveniently be radiopaque.

It is a further object to provide a method for producing an inorganic filler which is intended for use in polymerizable dental materials and for reinforcing plastic materials.

Another object of the invention is to provide a glass filler which equips composites with high reflection properties and good mechanical properties. It is a further object to provide a particulate glass filler which avoids the disadvantages of state of the art constructed agglomerates from different refractive index materials. Additionally, it is an object to provide glass fillers being a hybrid material for dental materials, in particular composites, with satisfactory gloss stability and advantageous handling at the same time.

Another object is to provide a glass filler which allows the possibility to charge composites with high amounts of fillers. In particular to provide composites or dental materials with satisfactory gloss stability, advantageous handling properties and with improved esthetic properties. Another object is to provide composites with good X-ray opacity as a result of charging them with high amounts of barium-containing glass fillers.

SUMMARY OF THE INVENTION

The invention in general concerns uniform filler particles having an identical refractive index, thermally welded together by sintering. More precisely it concerns particulate glass filler comprising glass particles, wherein the glass particles contain centrally located macro glass particles and on the outer surface of the macro particles micro glass particles are located, wherein the connection between macro and micro glass particles is of the material of said particles and, wherein the refractive index n of said particulate glass filler is in the range of n=1.50 to 1.60. The invention further concerns a method for producing the described glass particles, the particulate glass filler comprising said glass particles as well as a composite or dental material comprising the above particulate glass filler.

The glass particles according to the invention are agglomerates of macro particles and micro particles, wherein the micro particles are substantially located on the outer surface of the macro particles. Therefore, the glass filler of the invention belongs to agglomerated filler.

The claimed particulate glass filler is defined as a filling material for use in medical compositions, in particular for use in dental compositions such as composites and the like. High demands are made particularly on dental filler materials. They have to be abrasion and stain resistant and have to fulfill highest standards of aesthetically demands on tooth color and appearance. These requirements are fulfilled by the inventive particulate glass filler.

A glass filler material, which is dispersed and dried by special technology which make the amorphous glass filler particles keep a certain distance, is welded partly together by sintering under special temperature curve and forms a special micro-structure surface with retentive function. The filler body is of an amorphous and porous structure. Dental materials, in particular resin composite materials, with this filler are distinguished by special handling property and high gloss stability. Especially very small glass particles around 0.2 to 0.6 μm can be used to build very advantageous filler agglomerates with excellent gloss stability. Without the modification according to this invention, a high filler load cannot be achieved with this particle size. Such filler agglomerates provide a good level of radio-opacity. "Agglomerates" as used herein are the results of several particles having been welded together by sintering, in particular as described by the method according to the invention.

Dental materials, in particular composites, based on the agglomerated fillers (according to the invention) offer a permanent gloss stability and build a radio-opaque composite with advantageous handling properties (modeling behavior, shape stability)

DETAILED DESCRIPTION

In general, any glass filler particles may be used for the invention. Preferred are conventional dental glass fillers or materials used for the inventive particulate glass filler, for example made on the basis of boron silicate glass or aluminum silicate glass, such as glass made of barium borosilicate or lithium aluminium silicate and barium aluminium silicate, especially barium silicate dental glass fillers. Most preferred the particulate glass filler is comprising barium and/or strontium aluminium silicate dental glasses.

The particulate glass filler comprising glass particles, wherein the glass particles contain centrally located macro particles with connections to micro particles located on the outer surface of the macro particles, wherein the connections consist of the material of said particles, and wherein the refractive index n of the glass particles is in the range of n=1.50 to 1.60.

Macro particles according to the invention are particles having a particle size in the range of 200 nm to 1 μm, in particular in the range of 400 nm+/−200 nm.

Micro particles according to the invention are particles having a particle size in the range of 50 nm to 390 nm, in particular in the range of 200 nm+/−100 nm.

Particulate glass filler according to the invention are glass particles having a mean particle size in the range of 0.2 μm to 1.5 μm, in particular 400 nm+/−200 nm, wherein the glass particles contain centrally located macro particles with connections to micro particles located on the outer surface of the macro particles, wherein the connections consist of the material of said particles, and wherein the refractive index n of the glass particles is in the range of n=1.50 to 1.60.

Preferably the above described particulate glass filler comprises a connection consisting of the material of the macro particles. More preferably the particulate glass filler comprising glass particles comprises macro particles which are selected from dental glasses comprising barium and/or strontium. Most preferably the inventive particulate glass filler comprises macro particles selected from dental glasses comprising barium aluminum silicate and/or strontium aluminum silicate.

Preferred barium dental glass materials comprise at least 25 weight-% of BaO, in particular at least 30 weight-% of BaO, preferably at least 35 weight-% of BaO and barium aluminum silicate dental glass material comprise additionally to the amount of BaO at least 5 weight-% of $Al_2O_3$, in particular at least 8 weight-% of $Al_2O_3$, preferably at least 10 weight-% of $Al_2O_3$.

Preferred strontium dental glass materials comprise at least 10 weight-% of SrO, in particular at least 15 weight-% of SrO, preferably at least 25 weight-% of SrO and strontium aluminum silicate dental glass material comprise additionally to the amount of SrO at least 5 weight-% of $Al_2O_3$, in particular at least 10 weight-% of $Al_2O_3$, preferably at least 15 weight-% of $Al_2O_3$.

In a special embodiment the inventive glass filler with a refractive index n of the glass particles in the range of n=1.50 to 1.60 comprises macro particles made of dental glass comprising barium and/or strontium, preferably barium aluminum silicate and/or strontium aluminum silicate.

In an embodiment the particulate glass filler according to the invention comprises glass particles of macro particles selected from dental glasses having a transition temperature lower than 650° C. Dental glass materials comprising barium and/or strontium, preferably barium aluminum silicate and/or strontium aluminum silicate, having a transition temperature lower than 650° C. are preferred. Said materials having a refractive index n in the range of n=1.50 to 1.60 are mostly preferred.

In another embodiment of the invention the particulate glass filler comprises glass particles of macro particles having a refractive index n in the range of n=1.50 to 1.58. In particular these macro particles are preferably made of a dental glass material comprising barium and/or strontium and additionally, preferably barium aluminum silicate and/or strontium aluminum silicate, having a transition temperature lower than 650° C.

In a preferred embodiment the inventive particulate glass filler comprises glass particles of macro particles of a size in the range of 200 to 600 nm, in particular 400 nm+/−100 nm, more preferred +/−50 nm. In particular in the range of 300 to 500 nm, preferably +/−50 nm, preferably 400 nm+/−50 nm.

The inventive particulate glass filler comprises glass particles comprising micro particles having a refractive index n in the range of n=1.52 to 1.59. In particular said micro particles are connected to centrally located macro particles having a refractive index n in the range of n=1.50 to 1.58. Preferably this combination of micro and macro particles leads to glass particles of the inventive particulate glass filler. Most preferably the described combination is preferably used as the glass particles of the inventive particulate glass filler in curable dental materials and/or composites. The refractive index plays an important role for a good transparency of the dental materials.

In another embodiment of the invention the particulate glass filler comprising glass particles with micro particles selected from dental glass ceramics having a transition temperature higher than the transitions temperature of the macro particle dental glass material, in particular higher than 700° C., in particular higher than 750° C., higher than 800° C. Preferred embodiments of the inventive particulate glass filler comprises macro and micro particles wherein their transitions temperature differs by at least 50° C., preferably at least 70° C., most preferably at least 100° C. In particular macro particles made of barium and/or strontium, preferably barium and or strontium aluminum silicate dental glass material, exhibit a transition temperature higher than the dental glass ceramic material of the micro particles as described.

Suitable ceramic materials are nitride, carbide or oxide of the elements silicon, zirconium, aluminium, titanium, lithium, and/or lanthanum. $AL_2O_3$, $SiO_2$, $TiO_2$ $La_2O_3$, $ZrO_2$, $Li_2O$, $P_2O_5$ and MgO are preferred.

Glass-ceramics are polycrystalline materials produced through controlled crystallization of base glass. Glass-ceramic materials share many properties with both glasses and ceramics. Glass-ceramics have an amorphous phase and one or more crystalline phases and are produced by a so-called "controlled crystallization" in contrast to a spontaneous crystallization, which is usually not wanted in glass manufacturing. Glass-ceramics have the fabrication advantage of glass as well as special properties of ceramics. Glass-ceramics usually have between 30% [m/m] to 90% [m/m] crystallinity and yield an array of materials with interesting properties like zero porosity, high strength, toughness, translucency or opacity, low or even negative thermal expansion.

In another embodiment the inventive particulate glass filler comprises micro particles in the range of 100 to 300 nm, in particular 200 nm+/−50 nm, more preferred 180 nm, in particular +/−50 nm. In particular 130 nm, 140 nm, 150 nm, 160 nm, 170 nm, 180 nm, 190 nm, 200 nm, 210 nm, 220 nm or 230 nm.

In a preferred embodiment the inventive particulate glass filler comprising glass particles, preferably having a mean particle size of 0.2 μm to 0.7 μm, wherein the glass particles contain
    macro particles
        of dental glass comprising barium, preferably barium aluminium silicate,
        in the range of 400 nm+/−50 nm
        having a refractive index in the range of n=1.50 to 1.58, preferably n=1.55+/−0.01 and
        optionally having a transition temperature of lower than 650° C., preferably lower than 630° C., most preferably in the range of 630° C. to 580° C.

and
micro particles
of dental glass comprising ceramics,
in the range of 200 nm+/−50 nm,
having a refractive index in the range of n=1.50 to 1.58, preferably n=1.57+/−0.01 and
optionally having a transition temperature of greater than 700° C., in particular greater than 750° C., most preferably greater than 800° C.,
wherein macro particles are centrally located and said micro particles are connected to the outer surface of the macro particles. Preferably, the connection between the macro and micro particles is made of the material at least of the macro particles.

The connection between the macro and micro particles, in particular obtainable by sintering and welding these particles, is effected by the dental glass material(s) itself. More precisely the connection may be made of the dental glass material barium only, barium aluminum silicate only, strontium only, strontium aluminum silicate only, ceramics only or of a combination of at least two of the mentioned materials.

When strontium glass material is used, in particular strontium aluminum silicate, said material has a refractive index n=1.51+/−0.01.

The particulate glass filler according to the invention and the above described embodiments comprise glass particles in the range of 0.2 μm to 1 μm mean particle size, preferably in the range of 0.3 μm to 0.8 μm, more preferred 0.2 μm to 0.7 μm, most preferred in the range of 0.3 μm to 0.6 μm.

The above described inventive particulate glass filler comprising the described glass particles preferably is an amorphous and in particular porous glass filler.

Examples of commercially available dental glass particles without a limitation are those from SCHOTT comprising glass ceramics GM31684, GM31685, barium glasses GM27884, GM39923, G018-053, 8235, G018-186 and strontium glasses GM32087, G018-093 and G018-163. FIG. 1b a schematically image of the inventive glass filler comprising the above described dental glass particles, in particular representing the combination of GM27884 (refractive index n=1.52) as the centrally located macro particle and GM31685 (refractive index n=1.53) as the micro particles connected to GM27884. FIG. 1c a schematically image of state of the art particles with silica particles (refractive index 1.45) as the micro particles.

Another object of the invention is a method of producing particulate glass filler comprising glass particles according to the invention, as described above, wherein the method comprises the following steps, in particular particulate glass filler as described above obtainable by the method comprising the following steps:

I. Dispersing, in particular in a ball mill or other mixer suitable for mixing solids, glass filler with a refractive index n=1.5 to 1.60 with a suitable solvent, in particular the described macro and/or micro glass filler particles with a refractive index n=1.5 to 1.60 preferably with a ratio macro particles to micro particles of 1:1-4,
II. Sintering and welding the dispersed glass filler, in particular the dispersed macro and/or micro glass filler particles, at 450° C. to 800° C.,
III. Cooling the sintered glass filler, in particular the macro with thereto connected micro glass filler particles, to room temperature,
IV. Dispersing welded filler, preferably comprising macro and micro glass particles, wherein the micro particles are connected to the centrally located macro particles, in a suitable solvent, preferably an anhydrous alcohol, in particular in an ultrasonic dispersing machine, and
V. Drying of said glass filler, preferably performed in a vacuum cold drying machine, wherein a particulate glass filler comprising glass particles is obtained. In particular glass particles
are obtained which contain centrally located macro particles with connections to micro particles located on the outer surface of the macro particles, wherein the connections consist of the material of said particles, and wherein the refractive index n of the glass particles is in the range of n=1.50 to 1.60. Most preferably an amorphous particulate glass filler is obtained.

The solvent used in step I is preferably a mixture of water and alcohol, more preferably water and 0.01 wt-% to 1 wt-% alcohol, most preferably 0.1 wt-% alcohol with regard to the total of the mixture. The Dispersing step is preferably performed for 24 hours at 30 rpm (see example 1 below).

Before sintering (step II) the dispersed particles may be dried, preferably in a vacuum cold drying machine. Step I results in amorphous glass filler particles of certain distance.

In general, the particles are first subjected to a dispersion process in order to make the individual particles keep a distance from each other. This is preferably done by grinding with a suitable solvent.

After removal of the solvent after step I the fillers are advantageously sintered together by thermal treatment (welding, step II).

In a preferred embodiment of the above method the sintering (step II) is carried out at 500° C. to 770° C., more preferably from 600° C. to 750° C. The sintering is carried out preferably for 1 to 3 hours. In an embodiment of the inventive method the sintering and welding step is performed by the following temperature curve:

heating up from room temperature to 600° C. (5° C./minute) then to 700° C./710° C./720° C. (2° C./minute) and keep this temperature for 2 hours;
cooling from to 700° C./710° C./720° C. to 300° C. (2° C./minute) and
cooling naturally to room temperature (step III).

In the above method the treatment of step IV preferably takes 24 hours, in particular in anhydrous alcohol. After step IV amorphous and porous glass filler comprising glass particles of certain distance with retentive function are achieved.

Optionally silanization of the particulate glass filler, in particular performing salinization of the glass filler after step IV before drying, can be carried out. Silanization preferably is performed in a rotary evaporator. The slurry with an anhydrous alcohol and the welded filler are filled into the rotary flask, a suitable silane hydrolysate is added and followed by evaporating the alcohol (calculation of silane hydrolysate: 0.00965×weight of silanzed filler×surface area). Finally, silanized inventive particulate glass filler is removed from the flask and grinded, in particular by special rolling machine, and then sieving, preferably through a 100 mesh sieve, and keep it about 12 hours before final drying (step V). Thus, a silanized particulate glass filler comprising glass particles, wherein the glass particles contain centrally located macro particles with connections to micro particles located on the outer surface of the macro particles, wherein the connections consist of the material of said particles, and wherein the refractive index n of the glass particles is in the range of n=1.50 to 1.60.

In another embodiment the inventive method comprises the steps
Steps I to V as described above,
steps VI is preformed by
VI A treating the slurry with a suitable silane hydrolysate followed by evaporating the alcohol;
VI B grinding in a rolling machine;
VI C sieving, optionally through a 100 mesh sieve;
VI D optionally keeping the product for about 12 hours;
VI E and finally drying.

A most preferred embodiment of the inventive method comprises
Step I: Dispersing 3 kg glass filler into the miller (10 L) with 5 mm $ZrO_2$ ball 12 kg and plus 3200 g water and 0.1% alcohol, 30 rpm for 24 hours,
Drying the glass filler in a vacuum drying machine,
Step II-III: Sintering and welding using the above described temperature curve using Nabertherm N30/85HA,
Step IV: Dispersing by means of a special ultrasonic dispersing machine with 150 g of the welded filler in 1750 ml anhydrous alcohol, wherein the dispersing takes 24 h,
Silanization as described above with a suitable silane hydrolysate, and
Step V: Drying under 105° C. for 8 hours.

Another object of the invention is a method of improving gloss stability while maintain abrasions resistance in dental composite materials by incorporating therein a particulate glass filler comprising glass particles, wherein the glass particles contain centrally located macro particles with connections to micro particles located on the outer surface of the macro particles, wherein the connections consist of the material of said particles, and wherein the refractive index n of the glass particles is in the range of n=1.50 to 1.60.

By means of the described method particulate glass filler as previously described, in particular providing high gloss, improved translucency and advantageous radio-opacity of the resulting dental materials, is achieved.

The sintering temperature depends on the type of the glass filler particles and generally is between 450° to 1000° C. The temperature is selected such that during sintering the particles start to melt. Preferably, the macro particle starts to melt so that the micro particle will be retained when the micro particles adhere to the melted surface of the macro particle. At this point the macro particles only start to melt whereas micro particle keep solid because of their higher transition temperature. Consequently, the connection between the centrally located macro particle and bound micro particles is preferably built of the dental glass material of said macro particle as described above.

In principle, any amorphous glass filler with a particle size of 0.2 to 0.6 µm will be suitable. It may be commercially acquired as such, or produced by milling and sieving coarser glass particles.

When the suitable solvent is an alcohol, it is preferably a low boiling alcohol such as ethanol, propanol or isopropanol. Ethanol is preferred.

Suitable silane hydrolysates are known to the art-skilled person. 3-methacryloxypropyl-trimethoxysilane is preferred. The inventive welded fillers, in particular obtainable by the inventive method as described above, may be used in dental composites, suitably in amounts from 60 to 80, preferably from 65 to 75% by weight of the uncured composition.

Figure 1A:
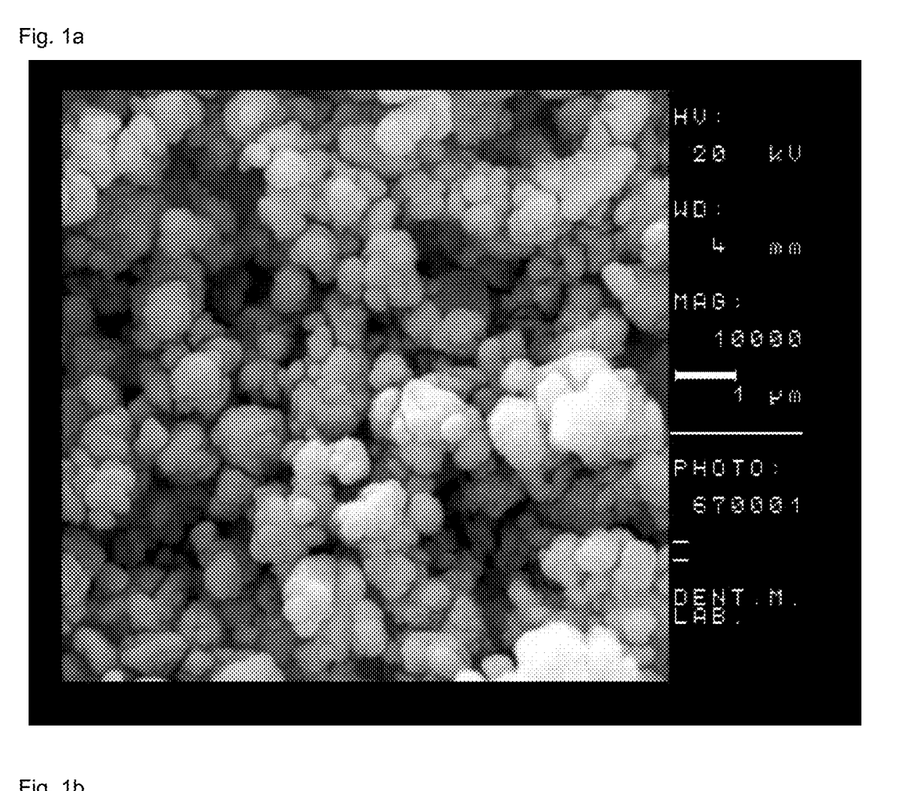
FIG. 1a is an REM photograph of the inventive filler particles sintered together, as described in Example 1.
Figure 1B:
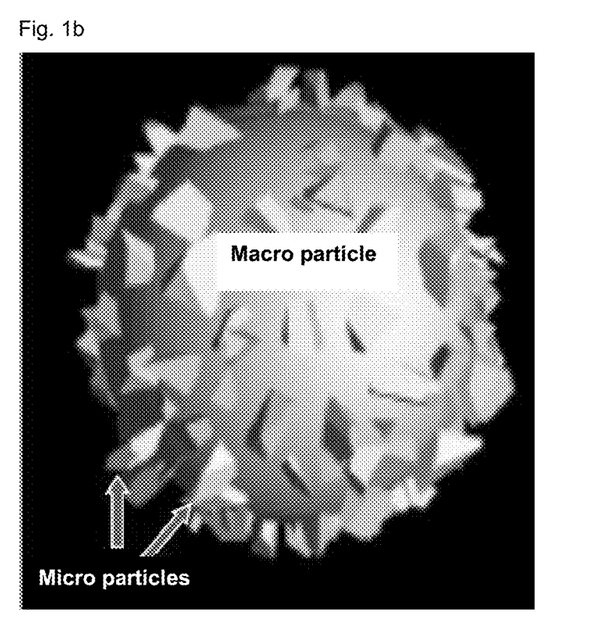
FIG. 1b is a more detailed schematically image of inventive filler particles sintered together, as described in Example 1.
Figure 1C:
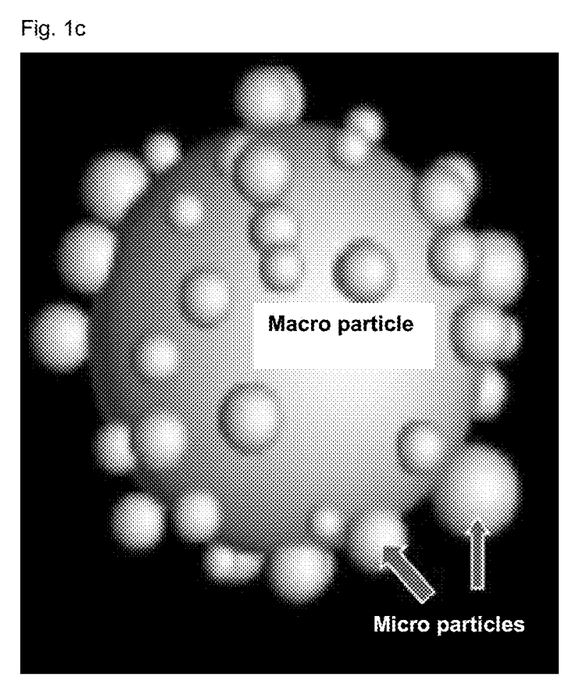
FIG. 1c is a detailed schematically image of state of the art filler particles sintered together.

The statements made in regard to the micro-structure of the filler particles and their anchoring in the matrix as illustrated by the transmission electron micrograph shown in FIG. 1a and the detailed schematically image in FIG. 1b compared to the state of the art filler shown in FIG. 1c. The bright zones in FIG. 1a represent the filler particles, the dark zones the polymer matrix. It is evident that the shape of the filler particles gives many possibilities for anchoring in the matrix.

The use of the above described inventive particulate glass filler, obtainable by the above described method, in dental materials, in particular in composites, is also an object of the invention.

A further object of the invention is a dental material comprising the above described particulate glass filler comprising glass particles, wherein the glass particles contain centrally located macro particles of the above characteristics and micro particles of the above characteristics, wherein these micro particles are connected to the outer surface of the macro particles, or at least a glass filler obtainable by the above described method, wherein the dental material is an uncured or cured material.

Preferably said inventive dental material possesses a gloss level greater than 30, in particular greater than 35, more particular greater than 40, 45, in the cured material.

Preferably said inventive dental material possesses a reflection level greater than 4%, in particular greater than 4.5, more particular greater than 5.0, 6.0, in the cured material.

Preferably said inventive dental material possesses a gloss level greater than 40, in particular greater than 45, in combination with a reflection level greater than 5%, in particular greater than 6.0% in the cured material. For example an embodiment of the inventive dental material comprising the above described glass filler having as the central macro particle GM27884 with a particle size of 0.4 µm and GM31684 with a particle size of 0.18 µm as the micro particle located on the outer surface of said macro particle exhibits a gloss level greater than 45 and an a reflection of greater than 6.0 (FIG. 1a, 1b).

Advantages of dental materials, curable or cured, containing fillers according to the invention are:
non slumping consistency and advantageous workability;
fast polishability;
high mechanical strength, as expressed by flexural strength and Young's modulus;
low abrasion, as expressed by roughness values,
high gloss stability, in particular permanent gloss stability, as expressed by high reflection, and
build a radio-opaque dental material with advantageous handling properties, in particular modelling behavior and shape stability.

Furthermore, as the invention allows higher filler loads compared to conventional fillers, it provides a way to raise X-ray opacity by using higher total amounts of barium-containing dental glass filler.

To explain the invention in detail, the production of a particulate composite filler in accordance with the invention and a formulation containing the composite filler for use as a dental material which can be polymerized by irradiation with light will be described in the examples which follow. The flexural strength of the different cured dental materials with and without fillers according to the invention will be determined and compared. The values of Young's modulus, mean roughness and reflection will be presented. All percentages are by weight unless otherwise indicated.

EXAMPLES

Methods
Method for Measuring Gloss Level of Dental Materials

A gloss testing device was used (angle 60°) from BYK Gardner GmbH (82538 Geretsried, Germany). The mean value was achieved from 5 measurements per sample.

Method for Measuring Reflection Level of Dental Materials

A surface laser scanner system (OPM GmbH, 76275 Ettlingen, Germany) was used to analyse the surface structure and roughness. The reflection degree of the laser beam was used to evaluate the surface reflection level. The resolution was set to 100 P/mm.

Tooth brush abrasion and ACTA method (poppy seed) were performed as described in ISO-TS14569-1/-2. The results are summarized in the following table 2 and 3.

Example 1

Production of the Filler

Step 1: Milling

Equipment: ball milling machine (the composition of the milling tank is the same basically as the glass filler) Process: put 3 kg glass filler into the miller (10 L) with 5 mm ZrO2 balls (12 kg), add 3200 g distilled water and 0.1% alcohol, rotate at 30 rpm for 24 hours;

Step 2: Drying of the glass filler:

The milled glass filler obtained in step 1 is dried in a conventional vacuum cold drying machine.

Step 3: Sintering and welding process:

Equipment: Nabertherm N30/85HA air circulation chamber furnace

Process: The product obtained in step 2 is introduced into the furnace and heated up from the room temperature to 600° C. (5° C./minute) then to 700° C./710° C./720° C. (2° C./minute) and kept at this temperature for 2 hours; followed by cooling from 700° C./710° C./720° C. to 300° C. (2° C./minute) and cooling naturally to room temperature Step 4: Dispersing welded filler Equipment: special ultrasonic dispersing machine.

Process: put 150 g of the welded filler obtained in step 3 into 1750 ml anhydrous alcohol and disperse for 24 hours.

Step 5: Production of silanized filler

Equipment: rotary evaporator.

Process: Put the slurry with anhydrous alcohol with the welded filler as obtained in step 4 into the rotary flask, add suitable silane hydrolysate and evaporate alcohol (calculation of silane hydrolysate:0.00965×weight of silanized filler×surface area); take out the filler from flask, grind by conventional rolling machine followed by sieving (100 mesh); keep for about 12 hours; put into drying cabinet at 105° C. for 8 hours.

Example 2

Tests in Composite Dental Material BHB, GM #201103

Filler containing dental composite pastes wherein conventional fillers are exchanged for different fillers and filler combinations as shown below were mixed and polymerized by light in the presence of photoinitiators as known in the art. The compositions of the dental materials are summarized in table 1 below.

Figure 2:
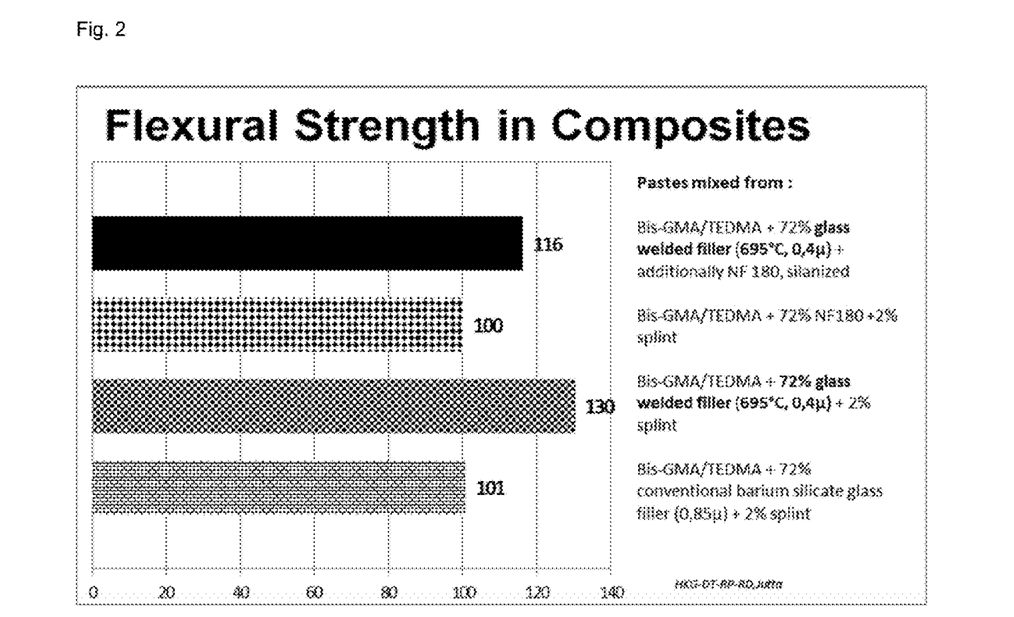
FIG. 2 is a diagram showing the flexural strength of composites of the invention, compared to composite outside the invention.
Figure 3:
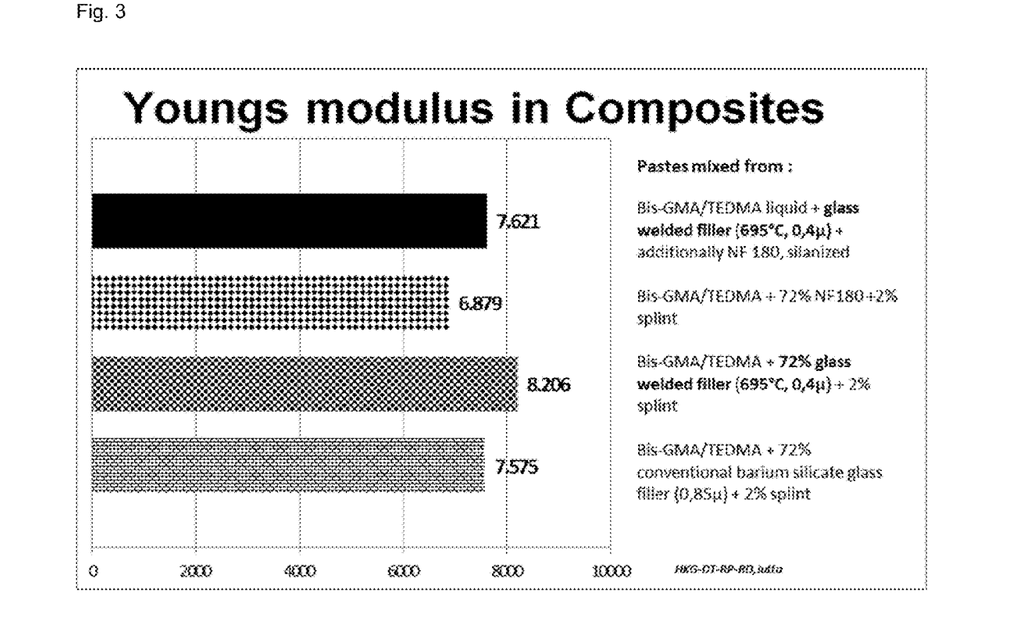
FIG. 3 is a diagram showing Young's modulus of composites of the invention, compared to composite outside the invention.

Ingredients for the Test Results Displayed in FIGS. 2 and 3
Bis-GMA: bisphenol-A-(di)methacrylate
TEDMA, also known as TEGDMA: triethylenglycol-dimethacrylate
NF 180: Very fine glass filler, grain size d50=180 nm, by Schott, Germany, particle size distribution: d50: 180+/−30 nm, d99>/=500 nm
Glass welded filler (695° C., 0.4p): Conventional barium silicate glass filler particles, mean diameter of the center particle is 0.4 µm, welded in analogy to Example 1 at 695° C.
Pre-polymer (or splint") Grinded polymer particles containing silanized pyrogenic silica, polymerized in the presence of a crosslinking methacrylate.

TABLE 1

| | compositions | | | |
|---|---|---|---|---|
| | VP110516/ 3 Ju [wt.-%] | VP110511/ 1 Ju [wt.-%] | VP110516/ 1 Ju [wt.-%] | 201103 [wt.-%] |
| Bowen | 18.12 | 18.12 | 18.12 | 17.77 |
| TEDMA | 7.77 | 7.77 | 7.77 | 7.62 |
| Campherchinon | 0.05 | 0.05 | 0.05 | 0.05 |
| Genocure EHA | 0.06 | 0.06 | 0.06 | 0.06 |
| GM 27884 UF sil.200 µm/Kulzer | 72.01 | 0 | 0 | 0 |
| Silanized self-welding filler. based on GM 27884 (d50 ~0.4 µm). welding temperature 695° C. | 0 | 72.00 | 0 | 55.88 |
| GM27884 NF 180-SiO3 | 0 | 0 | 72.00 | 18.63 |
| Estic Microfill Splitter | 2.00 | 2.00 | 2.00 | 0 |
| total | 100.00 | 100.00 | 100.00 | 100.00 |

The Glass Filler was Prepared by the Following Method

Step I: Dispersing 3 kg glass filler into the miller (10 L) with 5 mm ZrO₂ ball 12 kg and plus 3200 g water and 0.1% alcohol, 30 rpm for 24 hours. A ball milling machine was used, wherein the component of the milling tang is the same basically as the glass filler.

Drying the glass filler in a vacuum drying machine,

Step II-III: Sintering and welding was performed by means of Nabertherm N30/85HA with the following temperature curve:

heating up from room temperature to 600° C. (5° C./minute) then to 700° C./710° C./720° C. (2° C./minute) and keep this temperature for 2 hours;

cooling from to 700° C./710° C./720° C. to 300° C. (2° C./minute) and cooling naturally to room temperature (step III).

Step IV: Dispersing by means of a special ultrasonic dispersing machine with 150 g of the welded filler in 1750 ml anhydrous alcohol, wherein the dispersing takes 24 h, Silanization of the particulate glass filler was carried out in a rotary evaporator. The slurry with an anhydrous alcohol and the welded filler was filled into the rotary flask, a suitable silane hydrolysate was added and followed by evaporating the alcohol (calculation of silane hydrolysate: 0.00965×weight of silanzed filler× surface area). Finally, silanized inventive particulate glass filler was removed from the flask and grinded in a rolling machine and then was sieved through a 100 mesh sieve, and kept for about 12 hours before final drying (step V).

Step V: Drying at 105° C. for 8 hours.

The following composite pastes were polymerized and subjected to mechanical testing:

Pastes mixed from:

Bis-GMA/TEDMA liquid+glass welded filler (675° C., 0.4 μm)+additionally NF 180, silanized Bis-GMA/TEDMA+72% NF 180+2% pre-polymer filler Bis-GMA/TEDMA+72% glass welded filler (675° C., 0.4 μm)+2% pre-polymer filler Bis-GMA/TEDMA+72% conventional barium silicate glass filler (0.85 μm)+2% pre-polymer filler (reference)

Ingredients for the Rest Results Displayed in FIGS. 4 to 7

% Pre-polymer: as described above;

% 0.85 μm: conventional barium silicate glass filler, mean particle diameter 0.85 μm % 0.4 μm filler welded at various temperatures according to the invention % 0.85 μm filler welded at various temperatures outside the scope of to the invention NF 180 as described above Bis-GMA/TEDMA monomer composition 70:30 as described above.

Further Abbreviations:

GM and 6 digit numbers: various batches

BHB abbrevation for Heraeus affiliate company

The following pastes were polymerized; and reflection and roughness were determined.

| | | |
|---|---|---|
| BHB, GM, VP110516/3Ju | VP110516/3Ju: 0.85 μm glass particles |
| (72% 0.85 μm + 2% Pre-polymer) | not welded, |
| BHB, GM, VP110329/1Ju | VP110329/1Ju: 0.85 μm glass particles |
| (70% 0.85 μm + 5% Pre-polymer) | not welded |
| BHB, GM #20100723 | 20100723 0.85 μm glass particles welded |
| (76.5% 0.85 μm/700° C. + 0.18 μm) | at 700° C. + 0.18 μm glass particles welded at 700° C. |
| BHB, GM VP101122/2 Ju, | VP101122/2Ju: 0.85 μm glass particles |
| (70% 0.85 μm/700° C. + 2% Pre-polymer) | welded at 700° C. |
| BHB, GM, VP110328/1Ju, | VP110328/1Ju: 0.85 μm glass particles |
| (70% 0.85 μm/700° C. + 5% Pre-polymer) | welded at 700° C. |
| BHB, GM, VP110329/3Ju, | VP110329/3Ju: 0.85 μm glass particles |
| (70% 0.85 μm/710° C. + 5% Pre-polymer) | welded at 710° C. |
| BHB, GM, VP110329/4Ju, | VP110329/4Ju: 0.85 μm glass particles |
| (70% 0.85 μm/730° C. + 5% Pre-polymer) | welded at 730° C. |
| BHB, GM #201103 | #201103 0.4 μm glass particles welded at |
| (56% 0.4 μm/695° C. + 18.5% 0.18 μm) | 695° C. within the scope of the invention |
| BHB, GM, VP110511/1Ju | VP110511/1Ju 0.4 μm: glass particles |
| (72% 0.4 μm/695° C. + 2% Pre-polymer) | welded at 700° C. |
| BHB, GM, VP110516/1Ju | Defined as below |
| (72% 0.18 μm + 2% Pre-polymer) | |
| BHB, GM, VP110329/2Ju | Defined as below |
| (70% 0.18 μm + 5% Pre-polymer) | |
| Durafill VS A2, # 010214 | Defined as below |
| (reference) | |

TABLE 2

Figure 4:
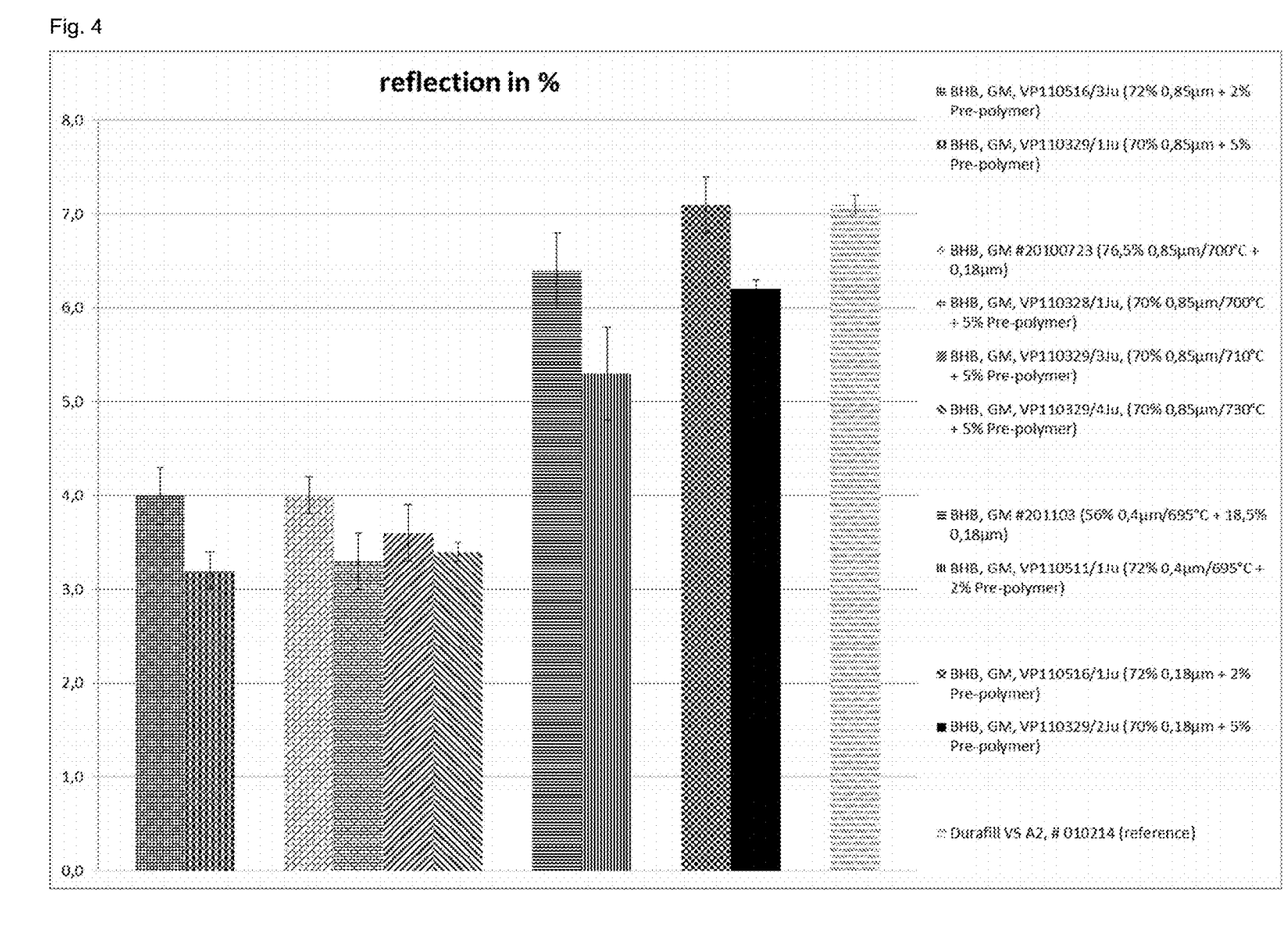
FIG. 4 is a diagram showing the reflection (tooth brush abrasion of composites of the invention, compared to composite outside the invention.
Figure 5:
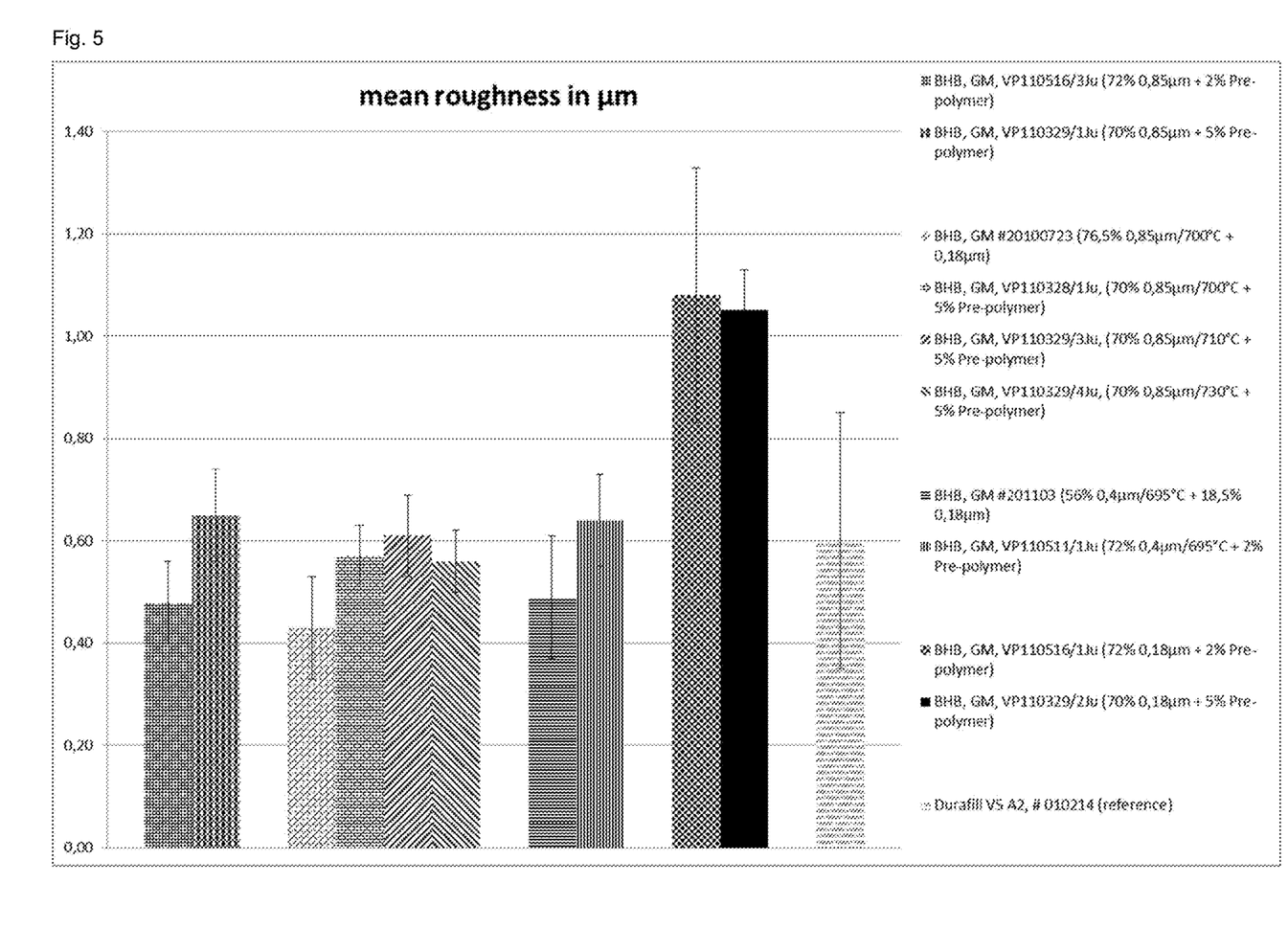
FIG. 5 is a diagram showing the mean roughness (tooth brush abrasion of composites of the invention, compared to composite outside the invention.

Tooth Brush Abrasion (see FIGS. 4 and 5)

| Material | GM27884 Particle size [μm] | Welding temperature [° C.] | Mean roughness [μm] | Reflection [%] | Gloss level |
|---|---|---|---|---|---|
| BHB, GM, VP110516/3Ju (72% 0.85 μm + 2% Pre-polymer) | 0.85 | | 0.48 | 4.0 | 15.8 |
| BHB, GM, VP110329/1Ju (70% 0.85 μm + 5% Pre-polymer | 0.85 | | 0.65 | 3.2 | 11.4 |
| BHB, GM #20100723 (76.5% 0.85 μm/700° C. + 0.18 μm) | 0.85 | 700 | 0.43 | 4.0 | 19.5 |
| BHB, GM, VP110328/1 Ju (70% 0.85 μm/700° C. + 5% Pre-polymer | 0.85 | 700 | 0.57 | 3.3 | 14.7 |
| BHB, GM, VP110329/3 Ju (70% 0.85 μm/710° C. + 5% Pre-polymer | 0.85 | 710 | 0.61 | 3.6 | 15.3 |
| BHB, GM, VP110329/4 Ju (70% 0.85 μm/730° C. + 5% Pre-polymer according to the invention | 0.85 | 730 | 0.56 | 3.4 | 14.1 |
| BHB, GM#201103 (56% 0.4 μm/695° C. + 18.5% 0.18 μm | 0.4 | 695 | 0.49 | 6.4 | 47.4 |
| BHB, GM, VP110511/1 Ju (72% 0.4 μm/675° C. + 2% Pre-polymer) | 0.4 | 695 | 0.64 | 5.3 | 37.5 |

TABLE 2-continued

Tooth Brush Abrasion (see FIGS. 4 and 5)

| Material | GM27884 Particle size [μm] | Welding temperature [° C.] | Mean roughness [μm] | Reflection [%] | Gloss level |
|---|---|---|---|---|---|
| BHB, GM, VP110516/1 Ju (72% 0.18 μm + 2% Pre-polymer) | 0.18 | | 1.08 | 7.1 | 31.9 |
| BHB, GM, VP110329/2 Ju (70% 0.18 μm + 5% Pre-polymer) | 0.18 | | 1.05 | 6.2 | 32.1 |
| Durafill VS, A2, #010214 (reference) | | | 0.60 | 7.1 | 36.5 |

TABLE 3

Figure 6:
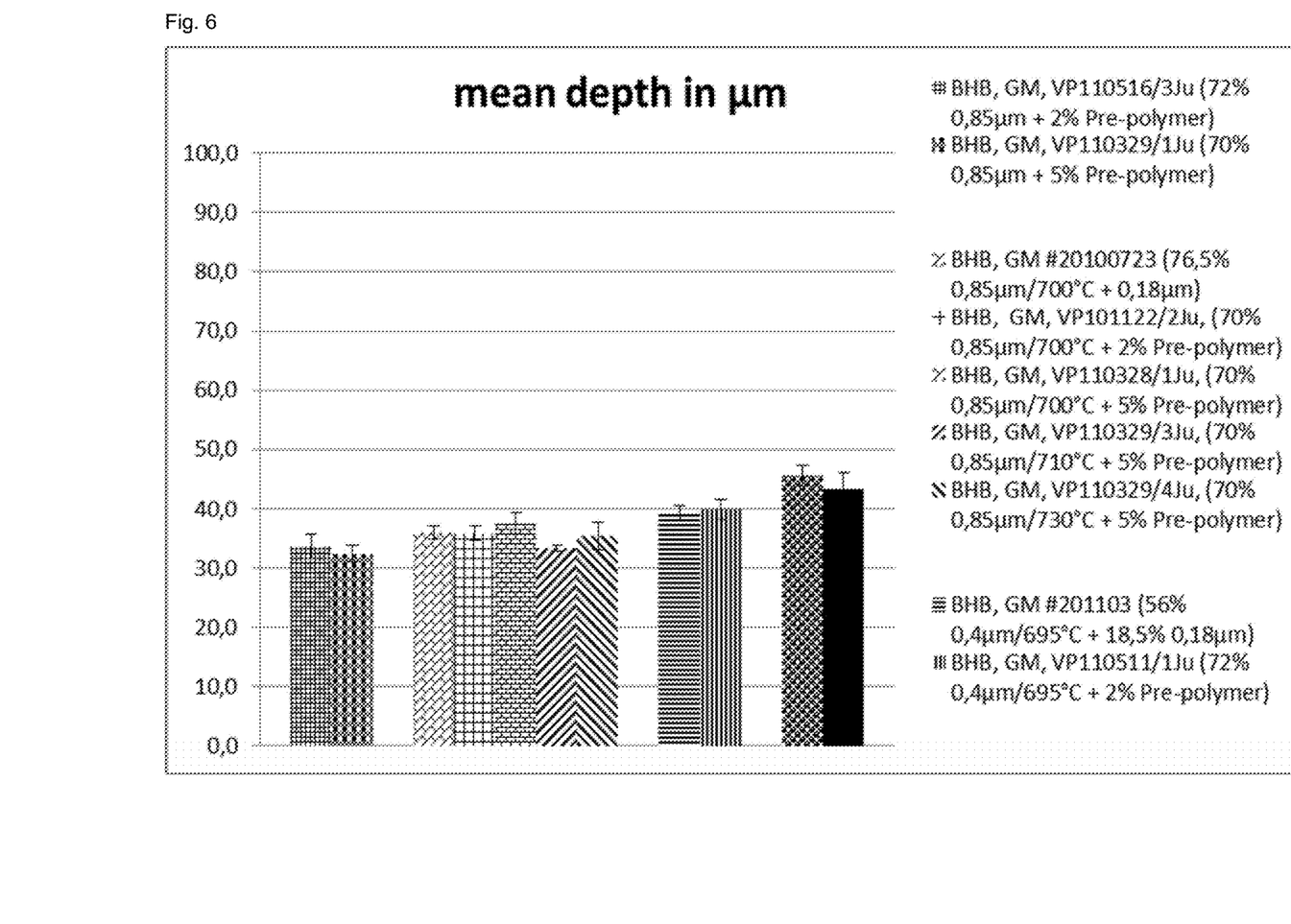
FIG. 6 is a diagram showing the mean depth (ACTA method (poppy seed)) of different filler materials as described in table 2, compared to glass filler of the invention.
Figure 7:
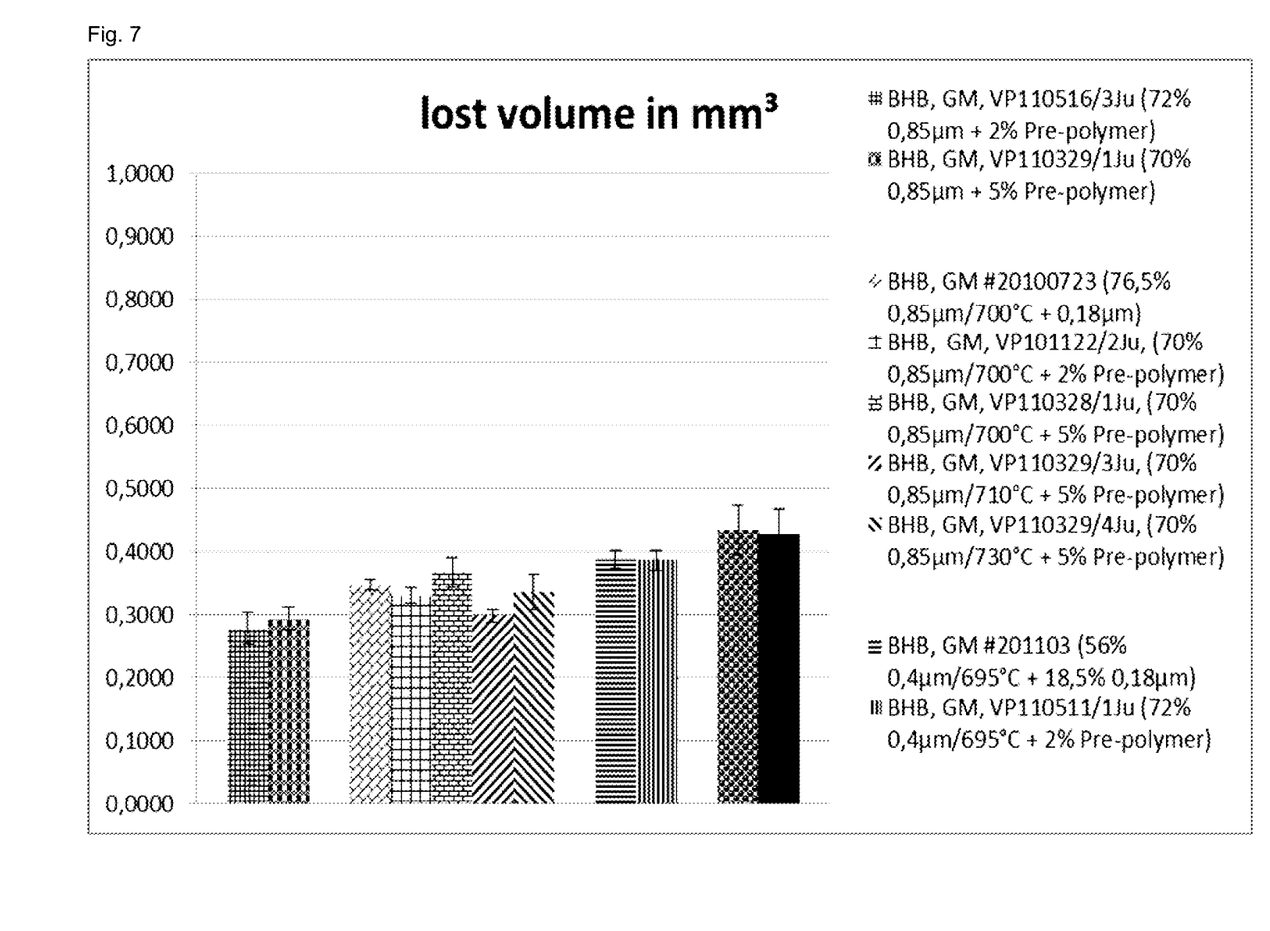
FIG. 7 is a diagram showing the lost volume (ACTA method (poppy seed)) of different filler materials as described in table 3 compared to glass filler of the invention.

ACTA method (poppy seed) (FIGS. 6 and 7)

| Material | GM27884 particle size [μm] | welding temperature [° C.] | Mean depth [μm] | Lost volume [mm³] |
|---|---|---|---|---|
| BHB, GM, VP110516/3Ju (72% 0.85 μm + 2% Pre-polymer) | 0.85 | | 33.6 | 0.2778 |
| BHB, GM, VP110329/1Ju (70% 0.85 μm + 5% Pre-polymer) | 0.85 | | 32.5 | 0.2939 |
| BHB, GM #20100723 (76.5% 0.85 μm/700° C. + 0.18 μm) | 0.85 | 700 | 36.0 | 0.3470 |
| BHB, GM, VP101122/2Ju, (70% 0.85 μm/700° C. + 2% Pre-polymer) | 0.85 | 700 | 35.9 | 0.3307 |
| BHB, GM, VP110328/1Ju, (70% 0.85 μm/700° C. + 5% Pre-polymer) | 0.85 | 700 | 37.5 | 0.3670 |
| BHB, GM, VP110329/3Ju, (70% 0.85 μm/710° C. + 5% Pre-polymer) | 0.85 | 710 | 33.4 | 0.2988 |
| BHB, GM, VP110329/4Ju, (70% 0.85 μm/730° C. + 5% Pre-polymer) | 0.85 | 730 | 35.4 | 0.3354 |
| according to the invention BHB, GM #201103 (56% 0.4 μm/695° C. + 18.5% 0.18 μm) | 0.4 | 695 | 39.3 | 0.3871 |
| BHB, GM, VP110511/1Ju (72% 0.4 μm/695° C. + 2% Pre-polymer) | 0.4 | 695 | 39.9 | 0.3865 |
| BHB, GM, VP110516/1Ju (72% 0.18 μm + 2% Pre-polymer) | 0.18 | | 45.6 | 0.4334 |
| BHB, GM, VP110329/2Ju (70% 0.18 μm + 5% Pre-polymer) | 0.18 | | 43.3 | 0.4271 |

Discussion of the Results: Flexural Strength and Young's Modulus (FIG. 2, FIG. 3):

The compositions within the scope of the invention comprising 0.4 μm filler according to the invention show superior values for of flexural strength and Young's modulus as compared to conventional filler materials. The filler-combination of welded filler according to the invention and pre-polymer (splint) is the strongest composition in both tests.

Discussion of Results: Mean Roughness and Reflection (FIG. 4, FIG. 5)

One can see that compositions a little outside the scope of the invention (1.8 μm, black and checked bars on the extreme right of the diagrams ▬▬ show good reflection values, but at the cost of high roughness.

In contrast the results for the compositions containing 0.4 μm welded filler according to the invention (horizontally and vertically striped bars on the right of the diagrams ▬▬ surprisingly provide optimal balancing of good abrasion resistance (i.e. low roughness) and good reflection. The remaining compositions represented by the first six bars from the left of the diagrams are state of the art compositions which show good abrasion resistance but low reflection values.

The glass filler [BHB, GM, VP110516/1 Ju (72% 0.18 μm+2% Pre-polymer] and [BHB, GM, VP110329/2 Ju (70% 0.18 μm+5% Pre-polymer] both show a good reflection of 6.2/7.1% but their mean roughness of 1.08/1.05 μm is not satisfactory (table 2).

[BHB, GM, VP110511/1 Ju (72% 0.4 μm/675° C.+2% Pre-polymer)] exhibits a worse reflection of 5.3% compared to the above described fillers but shows a lower mean roughness of 0.64%.

Durafill (reference) exhibits a good reflection of 7.1% but its mean roughness of 0.60 μm and gloss level of 36.5 are not as good as compared to the inventive glass filler.

In contrast the glass filler according to the invention [BHB, GM#201103 (56% 0.4 μm/695° C.+18.5% 0.18 μm] exhibits a good reflection of 6.4% and at the same time a very low mean roughness of 0.49 μm which is lower than the higher mean roughness values of previously described fillers.

Additionally, the inventive glass filler exhibits a gloss level of 47.4 which is significantly higher than the gloss level of [BHB, GM, VP110516/1 Ju (72% 0.18 μm+2% Pre-polymer], [BHB, GM, VP110329/2 Ju (70% 0.18 μm+5% Pre-polymer] or [BHB, GM, VP110511/1 Ju (72% 0.4 μm/675° C.+2% Pre-polymer)] with 31.9/32.1/37.5 (see table 2).

Thus, the inventive glass filler comprising macro glass particles of 0.4 μm and micro particles of 0.18 μm, obtained by the inventive method, surprisingly provides optimal balancing of an improved abrasion resistance (i.e. low roughness) and good reflection as well as a higher gloss level compared to the known fillers as described above.

The remaining compositions represented by the first six bars from the left of the diagrams are state of the art compositions which show comparable mean roughness (FIG. 5) with the inventive glass filler but low reflection values (FIG. 4) and significantly worse gloss values (table 2).

Discussion of Results: Mean Depth and Lost Volume (Table 3, FIGS. 6 and 7)

The glass filler according to the invention [BHB, GM#201103 (56% 0.4 μm/695° C.+18.5% 0.18 μm] exhibits a reduced depth of 39.3 μm and reduced lost of volume of 0.3871 mm$^3$ compared to state of the art glass filler combined with pre-polymer on the outer surface of the macro particles [BHB, GM, VP110516/1 Ju (72% 0.18 μm+2% Pre-polymer] and [BHB, GM, VP110329/2 Ju (70% 0.18 μm+5% Pre-polymer] showing a mean depth of 45.6/45.3 μm and lost of volume of 0.4334/0.4271 mm$^3$ (table 3).

Summary of Test Results

In summary the compositions with 0.4 μm welded glass particles show optimal balance between mechanical strength and reflection (gloss stability) and have very good mechanical strength.

The invention claimed is:

1. A particulate glass filler comprising glass particles, wherein
    the glass particles comprise centrally located macro glass particles with connections to micro glass particles located on an outer surface of the macro glass particles,
    wherein the connections consist of a material of said glass particles,
    wherein the glass particles have a refractive index n in the range of n=1.50 to 1.60, and
    wherein the macro glass particles have a size in the range of 200 to 600 nm.

2. The particulate glass filler according to claim 1, wherein the connections consist of a material of the macro glass particles.

3. The particulate glass filler according to claim 1, wherein the macro glass particles are selected from dental glasses comprising barium and/or strontium.

4. The particulate glass filler according to claim 1, wherein the macro glass particles are selected from dental glasses having a transition temperature lower than 650° C.

5. The particulate glass filler according to claim 1, wherein the macro glass particles have a refractive index n in the range of n=1.50 to 1.58.

6. The particulate glass filler according to claim 1, wherein the macro glass particles are selected from dental glasses comprising barium aluminum silicate glass and/or strontium aluminum silicate glass.

7. The particulate glass filler according to claim 1, wherein the micro glass particles have a refractive index in the range of n=1.52 to 1.59.

8. The particulate glass filler according to claim 1, wherein the micro glass particles are selected from dental glass ceramics having a transition temperature of greater than 700° C.

9. The particulate glass filler according to claim 1, wherein the micro glass particles have a size in the range of 100 to 300 nm.

10. The particulate glass filler according to claim 1, wherein the glass particles have a mean particle size in the range of 0.2 to 1.0 λm.

11. The particulate glass filler according claim 1, wherein the particulate glass filler is amorphous.

12. A method of producing a particulate glass filler according to claim 1 comprising the following steps:
    I. Dispersing glass filler with a refractive index n=1.50 to 1.60 with a suitable solvent;
    II. Sintering and welding the dispersed glass filler at 450° C. to 800° C.;
    III. Cooling the sintered glass filler to room temperature;
    IV. Dispersing welded filler in a suitable solvent;
    V. Drying of said glass filler; and
    VI. Obtaining a particulate glass filler comprising glass particles.

13. The particulate glass filler according to claim 1, wherein the macro glass particles have a size in the range of 400 nm±100 nm.

14. The particulate glass filler according to claim 1, wherein the macro glass particles have a size in the range of 400 nm±50 nm.

15. The particulate glass filler according to claim 8, wherein the micro glass particles are selected from dental glass ceramics having a transition temperature of greater than 750° C.

16. The particulate glass filler according to claim 8, wherein the micro glass particles are selected from dental glass ceramics having a transition temperature of greater than 800° C.

17. The particulate glass filler according to claim 9, wherein the micro glass particles have a size in the range of 200±5 nm.

18. The particulate glass filler according to claim 9, wherein the micro glass particles have a size in the range of 180±5 nm.

19. The particulate glass filler according to claim 10, wherein the glass particles have a mean particle size in the range of 0.3 to 0.6 μm.

20. The particulate glass filler according to claim 1, wherein both the macro glass particles and the micro glass particles have a refractive index n in the range of n=1.50 to 1.60.

* * * * *

UNITED STATES PATENT AND TRADEMARK OFFICE
CERTIFICATE OF CORRECTION

| | |
|---|---|
| PATENT NO. | : 9,642,781 B2 |
| APPLICATION NO. | : 14/888900 |
| DATED | : May 9, 2017 |
| INVENTOR(S) | : Wenling Yang et al. |

Page 1 of 1

It is certified that error appears in the above-identified patent and that said Letters Patent is hereby corrected as shown below:

In the Specification

Column 12, Line 8, "0.4p" -- should read -- 0.4μ --.

Column 14, Line 1, "Rest Results" -- should read -- Test Results --.

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*